United States Patent
Fu et al.

(10) Patent No.: US 11,639,502 B2
(45) Date of Patent: May 2, 2023

(54) MACROBRACHIUM NIPPONENSE CATHEPSIN L GENE, DSRNA THEREOF, AND USE THEREOF

(71) Applicant: Freshwater Fisheries Research Center, Chinese Academy of Fishery Sciences, Wuxi (CN)

(72) Inventors: Hongtuo Fu, Wuxi (CN); Hui Qiao, Wuxi (CN); Wenyi Zhang, Wuxi (CN); Sufei Jiang, Wuxi (CN); Yiwei Xiong, Wuxi (CN); Shubo Jin, Wuxi (CN); Yongsheng Gong, Wuxi (CN)

(73) Assignee: FRESHWATER FISHERIES RESEARCH CENTER, CHINESE ACADEMY OF FISHERY SCIENCES, Wuxi (CN)

( * ) Notice: Subject to any disclaimer, the term of this patent is extended or adjusted under 35 U.S.C. 154(b) by 0 days.

(21) Appl. No.: 17/752,002

(22) Filed: May 24, 2022

(65) Prior Publication Data

US 2022/0356477 A1 Nov. 10, 2022

Related U.S. Application Data

(63) Continuation of application No. PCT/CN2021/118232, filed on Sep. 14, 2021.

(30) Foreign Application Priority Data

Feb. 5, 2021 (CN) .......................... 202110161949.X

(51) Int. Cl.
*C12N 15/113* (2010.01)
*A61P 15/08* (2006.01)

(52) U.S. Cl.
CPC .......... *C12N 15/1137* (2013.01); *A61P 15/08* (2018.01)

(58) Field of Classification Search
CPC .................................................. C12N 15/1137
See application file for complete search history.

(56) References Cited

FOREIGN PATENT DOCUMENTS

| CN | 1675358 A | 9/2005 |
| CN | 112852846 A | 5/2021 |

OTHER PUBLICATIONS

Li et al. (Biochemistry & Molecular Biology (2018) vo. 218, pp. 1-12). (Year: 2018).*

Zhao,W. et. al. "Molecular characterization of cathepsin L cDNA and its expression during oogenesis and embryogenesis in the oriental river prawn Macrobrachium nipponense (Palaemonidae)" Genetics and Molecular Research, Oct. 30, 2013,vol. 4, 12,p. 5216-5223.

Zhao,Weihong, "Cloning and expression of the genes involving in the vitellogenin metabolisum inoriental river prawn. Macrobrachium nipponense", Doctoral dissertaton database, Jul. 15, 2011. v7, D052-8.

Onming, S. et al. Macrobrachium rosenbergii close SMbr00120 cathepsin L mRNA, partial cds, Genebank, KJ62234.1 NCBI Aug. 30, 2018.

Li, yundong et. al. "Cloning and expression analysis of cathepsin L cDNA of Penaeus monodon" South China Fishries Science, vol. 12 No. 3, Jun. 30, 2016.

Zhu, JP et. al. "Expression and functional analysis of cathepsin L1 in ovarian development of the oriental river prawn, Macrobrachium nipponense" Aquaculture Reports vol. 20 May 21, 2021.

Jiang, Hongxia et. al. "Molecular cloning and initial function analysis of cystatin gene in Macrobrachium nipponense" J. fishery Sciences of China. 25(5) Sep. 30, 2018.

Jiang, Hongxia et. al. "Insights into Sexual Precocity of Female Oriental River Prawn Macrobrachium nipponense through Transcriptome Analysis" PLOS ONE 6(11) Jun. 9, 2016.

H. Qiao et. al. "Gene expression profile analysis of testis and ovary of oriental river prawn, Macrobrachium nipponense, reveals candidate reproduction-related genes" Genetics and Molecular Research 12(1) Mar. 20, 2015.

* cited by examiner

*Primary Examiner* — J. E. Angell
(74) *Attorney, Agent, or Firm* — IPro, PLLC

(57) ABSTRACT

The present disclosure relates to the technical field of biology, and in particular to a *Macrobrachium nipponense* Cathepsin L gene and use of dsRNA thereof, including the *Macrobrachium nipponense* Cathepsin L gene, a gene fragment and the dsRNA thereof, and use of the dsRNA in inhibiting ovary development of *Macrobrachium nipponense*. The *Macrobrachium nipponense* Cathepsin L gene is obtained at first with the full-length nucleotide sequence as shown in SEQ ID No. 1 and the amino acid sequence as shown in SEQ ID No. 2. Gene fragments with sequences of SEQ ID No. 3 and SEQ ID No. 8 are obtained by using technologies such as RNA interference, and dsRNA1 and dsRNA2 are synthesized from the two gene fragments. The synthesized dsRNA1 and dsRNA2 are injected into a pericardial cavity of a female *Macrobrachium nipponense* and the result shows that the dsRNA1 can effectively slow down the ovary development speed of the female *Macrobrachium nipponense*.

6 Claims, 1 Drawing Sheet
Specification includes a Sequence Listing.

under the action of Dicer enzyme, and a target mRNA is finally degraded, resulting in that cells or individuals cannot synthesize corresponding amino acids, the functional expression of individuals is deficient, and the purpose of interference knockout is realized. It has been proved that the RNAi of a *Vitellogenin* gene of *Macrobrachium nipponense* can effectively inhibit ovary development of *Macrobrachium nipponense* (Bai et al., 2015). The RNAi technology has been proved to have a very good use prospect in solving the problem of "rapid sexual maturity" of the *Macrobrachium nipponense*.

MACROBRACHIUM NIPPONENSE CATHEPSIN L GENE, DSRNA THEREOF, AND USE THEREOF

The instant application contains a Sequence Listing in TXT format as a file named "seq.txt", created on Nov. 30, 2022, of 6 kB in size, and which is hereby incorporated by reference in its entirety.

TECHNICAL FIELD

The present disclosure relates to the technical field of biology and particularly relates to a *Macrobrachium nipponense* Cathepsin L gene, dsRNA thereof, and use thereof.

BACKGROUND

*Macrobrachium nipponense*, also commonly called as Oriental river prawn, belongs to genus *Macrobrachium*, family Palaemonidae, order Decapoda, class Crustacea, phylum Arthropoda. The *Macrobrachium nipponense* is widely distributed in fresh water and saline water areas in Asia and is one of the important freshwater prawns species in China. According to the statistics of China Fishery Statistical Yearbook in 2020, the yield of the *Macrobrachium nipponense* cultured in China in 2019 exceeded 220,000 tons. Female *Macrobrachium nipponense* rapidly reaches sexual maturity. During a breeding season, the young prawns can reach sexual maturity after hatching for about 45 days and the female prawns grown in the current year can reproduce for multiple generations. Particularly, in a period of summer with higher water temperature, an ovary maturation period of the female prawns only needs 15 days. This characteristic has plagued the industry of *Macrobrachium nipponense* for many years. The rapid maturity of the ovary leads to the over-rapid propagation of the *Macrobrachium nipponense*. Therefore, multiple generations exist in the same place, which may cause problems that the culture density is over-high, the oxygen deficiency risk is obviously increased, and the feed consumption is increased, thereby seriously affecting the economic benefit of culture, and bringing difficulties for scientific research such as family breeding. Therefore, it is of great significance for healthy and efficient development of the industry of *Macrobrachium nipponense* to find a method for controlling ovary development of *Macrobrachium nipponense* and inhibiting the rapid maturity of the ovary of the *Macrobrachium nipponense*.

Cathepsins are a class of proteolytic enzymes predominantly found in lysosomes and widely distributed within a variety of organisms. Cathepsin L is a major member of lysosomal cysteine proteases of papain family C1, plays an important role in physiological and pathological processes, and is mainly responsible for protein hydrolysis, such as antigen presentation, proteolysis, and tumor metastasis. During the physiological process, the Cathepsin L degrades exogenous proteins to produce polypeptide antigenic determinants to bind to major histocompatibility complex class II (MHC II) molecules to participate in the antigen presentation. During the pathological process, the Cathepsin L degrades extracellular matrix through proteolysis to promote tumor cell to penetrate through the extracellular matrix for metastasis.

In an RNA interference (RNAi) technology, a plurality of small RNA fragments are obtained by double-stranded RNA

SUMMARY

In view of this, the present disclosure provides a *Macrobrachium nipponense* Cathepsin L gene, a gene fragment and a dsRNA thereof, and use of the dsRNA in inhibiting ovary development of *Macrobrachium nipponense*. The gene can be used for slowing down the ovary development and maturation of female *Macrobrachium nipponense* and provide new ideas for solving the problem of "rapid sexual maturity" and conducting genetic improvement of *Macrobrachium nipponense*.

In order to realize the aforementioned objective of the present disclosure, the present disclosure provides the following technical solutions.

The present disclosure provides a *Macrobrachium nipponense* Cathepsin L gene, which has the following sequences:

(I) a nucleotide sequence as shown in SEQ ID No. 1; or (II) a nucleotide sequence encoding the same protein as the nucleotide sequence as shown in (I), but different from the nucleotide sequence as shown in (I) due to degeneracy of genetic codes; or (III) a nucleotide sequence obtained by substituting, deleting or adding one or more nucleotide sequences to the nucleotide sequence as shown in (I) or (II) and having the same or similar functions as the nucleotide sequence as shown in (I) or (II); or (IV) a nucleotide sequence having at least 90% sequence identity with the nucleotide sequence as shown in (I), (II) or (III).

On the basis, the present disclosure provides a protein encoded by the *Macrobrachium nipponense* Cathepsin L gene and the protein has the following sequences:

(I) an amino acid sequence as shown in SEQ ID No. 2; or (II) an amino acid sequence obtained by substituting, deleting or adding one or more amino acids to the amino acid sequence as shown in (I) and having the same or similar functions as the amino acid sequence as shown in (I); or (III) an amino acid sequence having at least 90% identity with the amino acid sequence as shown in (I) or (II).

More importantly, the present disclosure further provides use of the *Macrobrachium nipponense* Cathepsin L gene or the protein as a target in preparing an inhibitor for ovary development of *Macrobrachium nipponense*.

Based on the research, the present disclosure further provides a *Macrobrachium nipponense* Cathepsin L gene fragment, which has the following sequences:

(I) a nucleotide sequence as shown in SEQ ID No. 3; or (II) a nucleotide sequence encoding the same protein as the nucleotide sequence as shown in (I), but different from the nucleotide sequence as shown in (I) due to degeneracy of genetic codes; or (III) a nucleotide sequence obtained by substituting, deleting or adding one or more nucleotide sequences to the nucleotide sequence as shown in (I) or (II) and having the same or similar functions as the nucleotide sequence as shown in (I) or (II); or (IV) a nucleotide sequence having at least 90% sequence identity with the nucleotide sequence as shown in (I), (II) or (III).

The present disclosure further provides use of the *Macrobrachium nipponense* Cathepsin L gene fragment in preparing an inhibitor for ovary development of *Macrobrachium nipponense*.

In addition, the present disclosure further provides a primer set for amplifying the *Macrobrachium nipponense* Cathepsin L gene fragment and the primer set has the following sequences:

(I) an upstream primer has a nucleotide sequence as shown in SEQ ID NO. 4 and a downstream primer has a nucleotide sequence as shown in SEQ ID NO. 5;

(II) a nucleotide sequence obtained by substituting, deleting or adding one or more nucleotide sequences to the nucleotide sequence as shown in (I) and having the same or similar functions as the nucleotide sequence as shown in (I); or (III) a nucleotide sequence having at least 90% sequence identity with the nucleotide sequence as shown in (I) or (II).

Based on the provided primer set, the present disclosure provides a method for obtaining a *Macrobrachium nipponense* Cathepsin L interference gene fragment: after analyzing the amino acid sequence of *Macrobrachium nipponense* Cathepsin L, selecting a specific region of Cathepsin L and designing an interference primer, where the upstream primer is as shown in SEQ ID No. 4 and the downstream primer is as shown in SEQ ID No. 5; and conducting PCR amplification to obtain a DNA fragment as shown in SEQ ID No. 3 by using total cDNA of *Macrobrachium nipponense* as a template.

The present disclosure further provides a dsRNA, which is obtained by transcription using the *Macrobrachium nipponense* Cathepsin L gene fragment as a template.

The present disclosure further provides use of the dsRNA in inhibiting mRNA expression of the *Macrobrachium nipponense* Cathepsin L gene.

The present disclosure further provides use of the dsRNA in inhibiting ovary development of *Macrobrachium nipponense*.

The present disclosure further provides use of the *Macrobrachium nipponense* Cathepsin L gene and the dsRNA thereof, and includes the *Macrobrachium nipponense* Cathepsin L gene, a gene fragment and the dsRNA thereof, and use of the dsRNA in inhibiting ovary development of *Macrobrachium nipponense*. The *Macrobrachium nipponense* Cathepsin L gene is obtained at first with the full-length nucleotide sequence as shown in SEQ ID No. 1 and the amino acid sequence as shown in SEQ ID No. 2. Gene fragments with sequences of SEQ ID No. 3 and SEQ ID No. 8 are obtained by using technologies such as RNA interference, and dsRNA1 and dsRNA2 are synthesized from the two gene fragments. The synthesized dsRNA1 and dsRNA2 are injected into a pericardial cavity of a female *Macrobrachium nipponense* and the result shows that the dsRNA1 can effectively slow down the ovary development speed of the female *Macrobrachium nipponense*.

BRIEF DESCRIPTION OF FIGURES

In order to more clearly illustrate the examples of the present disclosure or the technical solutions in the prior art, the following will briefly introduce the drawings that need to be used in the description of the examples or the prior art.

DETAILED DESCRIPTION

Figure 1:
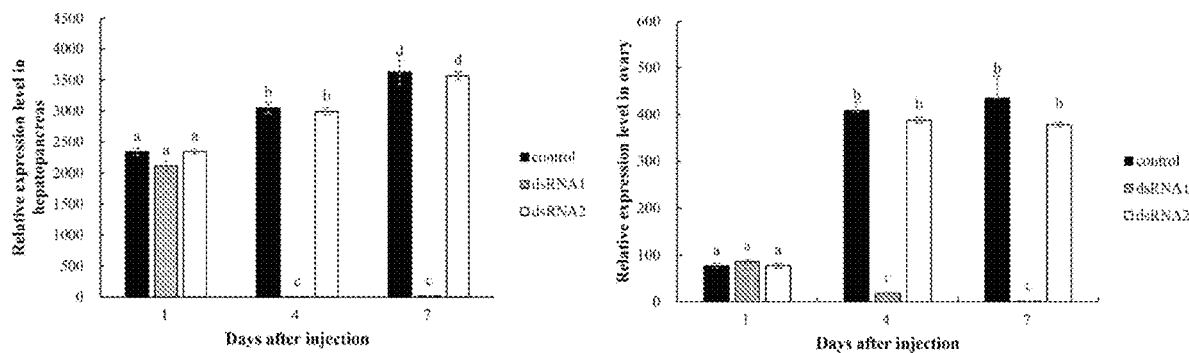
FIG. 1 shows the mRNA expression of a Cathepsin L gene in ovary and hepatopancreas at different sampling time points after injection of dsGFP, dsRNA1 and dsRNA2 into female *Macrobrachium nipponense* at an ovary development stage I, where a *Macrobrachium nipponense* β-Actin gene is used as an internal reference gene; 1, 4 and 7 are the 1st, 4th, and 7th days after injection respectively (n=9); and different letters represent $p<0.05$. A green fluorescent protein (GFP) gene is used as a reporter gene in a control group and the *Macrobrachium nipponense* in the control group is injected with the same dose of dsGFP.

The present disclosure discloses a *Macrobrachium nipponense* Cathepsin L gene, a gene fragment and a dsRNA thereof, and use of the dsRNA in inhibiting ovary development of *Macrobrachium nipponense*. Those skilled in the art can learn from the content of this document and appropriately improve process parameters. Of particular note, all similar substitutions and alterations will be apparent to those skilled in the art, and they are all deemed to be included in the present disclosure. The method and use of the present disclosure have been described through preferred embodiments. It is obvious that relevant persons can make modifications or appropriate alterations and combinations to the method and use described herein without departing from the content, spirit and scope of the present disclosure to achieve and use the technology of the present disclosure.

The present disclosure provides a *Macrobrachium nipponense* Cathepsin L gene whose nucleotide sequence is as shown in SEQ ID No. 1 and amino acid sequence is as shown in SEQ ID No. 2.

The present disclosure provides a high-efficiency *Macrobrachium nipponense* Cathepsin L interference gene fragment whose nucleotide sequence is as shown in SEQ ID No. 3.

The present disclosure provides a method for obtaining a *Macrobrachium nipponense* Cathepsin L interference gene fragment: after the amino acid sequence of *Macrobrachium nipponense* Cathepsin L is analyzed, a specific region of Cathepsin L is selected and two pairs of interference primers are designed: one interference primer pair has an upstream primer as shown in SEQ ID No. 4 and a downstream primer as shown in SEQ ID No. 5; and the other interference primer pair has an upstream primer as shown in SEQ ID No. 6 and a downstream primer as shown in SEQ ID No. 7; and then PCR amplification is conducted to obtain DNA fragments SEQ ID No. 3 and SEQ ID No. 8 by using total cDNA of *Macrobrachium nipponense* as a template.

Further, the DNA fragments SEQ ID No. 3 and SEQ ID No. 8 are used as templates, and dsRNA1 and dsRNA2 are synthesized by using kits.

Use of dsRNA1 and dsRNA2 synthesized by using the DNA fragments SEQ ID No. 3 and SEQ ID No. 8 as templates in inhibiting ovary development of female *Macrobrachium nipponense*: the dsRNA1 and the dsRNA2 are injected into the pericardial cavity of the *Macrobrachium nipponense* at the injection concentration of 4 μg/g. Results show that injection of the dsRNA1 synthesized with SEQ ID No. 3 as the template can effectively reduce the mRNA expression of the *Macrobrachium nipponense* Cathepsin L gene and inhibit the ovary development speed of *Macro-* brachium nipponense. But the injection of the dsRNA2 synthesized with SEQ ID No. 8 as the template does not effectively reduce the mRNA expression of the *Macrobrachium nipponense* Cathepsin L gene and does not inhibit the ovary development speed of the *Macrobrachium nipponense*.

Where:

SEQ ID No. 1
ttgaaatctcccgttcaataaacattttctccacaactacgattctcta
atccgagactttccgcagatgaaattcctgctcttcctctgtggtttgg
ccatcgctgccgccagtcagtcatgggaaagctttaagctgacccatgg
caaggcctactccaacgccaaggaggagctctacaggaagaccattttc
gagagcaaccttaaattcgtagcagaacacaatgaacgcttccgaaagg
gcctagtcaccttcaacgtcgccatgaacagatttggtgacttgaccac
agaggagtttgtagcccagatgactggtctgcagaaactggagagcacc
gagggaatggaattcgctcacttccctgaggccccagagctgccgatg
ttgactggagaaacaagggagctgtcactcctgtcaaggaccagggaca
gtgtggatcctgctggtccttctctactactggagctctagaaggcgca
catttcatcaaaaccggaagtctgccaagcctctccgaacagcagctgg
ttgattgctcaaaggaaaacagcggttgcaacggaggagttgtgcaatg
ggcctacgattacctcaagtcctgcggaggaagccagactgagtcttcc
tatccttacgaggctattgacaacatatgccgcttcgattcatctcagg
tggctgccactgtgaggggatacacgaacatcccctatggcgatgaggt
gactcaggcctctgctgtccacgacgaaggtccagtcagtgtctgcgtc
gatgctggacacttgtccttccagttgtacagctcaggtgtctactacg
aaccaaactgcaaccctcagggcatcaaccacgccgtgttggctgttgg
ctacggaaccgaaggcggctccgactactggatcatcaagaactcgtgg
ggcagcagctggggtgagtctggatacatgaagctcaccaggaacaaga
acaaccactgcggtgttgccacccagtcttgctacccaaccgtctaagg
attccaagaaagtctggttgctttattccatgaagagttatgagtatac
atcgacaccttaactcataagaccatagcttgataatcatgtctggctt
tatatcttgtttatgaaaaataaagtggaatcgattaaaaaaaaaa SEQ ID No. 2
MKFLLFLCGLAIAAASQSWESFKLTHGKAYSNAKEELYRKTIFESNLKF
VAEHNERFRKGLVTFNVAMNRFGDLTTEEFVAQMTGLQKLESTEGMEFA
HFPEAPRAADVDWRNKGAVTPVKDQGQCGSCWSFSTTGALEGAHFIKTG
SLPSLSEQQLVDCSKENSGCNGGVVQWAYDYLKSCGGSQTESSYPYEAI
DNICRFDSSQVAATVRGYTNIPYGDEVTQASAVHDEGPVSVCVDAGHLS
FQLYSSGVYYEPNCNPQGINHAVLAVGYGTEGGSDYWIIKNSWGSSWGE
SGYMKLTRNKNNHCGVATQSCYPTV SEQ ID No. 3
gctctacaggaagaccattttcgagagcaaccttaaattcgtagcagaa
cacaatgaacgcttccgaaagggcctagtcaccttcaacgtcgccatga acagatttggtgacttgaccacagaggagtttgtagcccagatgactgg
tctgcagaaactggagagcaccgagggaatggaattcgctcacttc SEQ ID No. 4
gctctacaggaagaccattttc SEQ ID No. 5
gaagtgagcgaattccattcc SEQ ID No. 6
gcctacgattacctcaagtcc SEQ ID No. 7
gtggacagcagaggcctgagtc SEQ ID No. 8
gcctacgattacctcaagtcctgcggaggaagccagactgagtcttcct
atccttacgaggctattgacaacatatgccgcttcgattcatctcaggt
ggctgccactgtgaggggatacacgaacatcccctatggcgatgaggtg
actcaggcctctgctgtccac In the *Macrobrachium nipponense* Cathepsin L gene, the gene fragment and the dsRNA thereof, and the use of the dsRNA in inhibiting ovary development of *Macrobrachium nipponense* provided by the present disclosure, all of the raw materials and reagents used can be purchased from the market.

The present disclosure will be described in detail below in connection with specific examples:

Example 1 Obtaining of Full-Length Sequence of *Macrobrachium nipponense* Cathepsin L Gene Transcriptomes at each ovary development stage of female *Macrobrachium nipponense* were compared and analyzed, thus a full-length differential Cathepsin L gene was obtained with the full-length nucleotide sequence of SEQ ID No. 1 and the amino acid sequence of SEQ ID No. 2.

Example 2 Obtaining of *Macrobrachium nipponense* Cathepsin L Gene Fragment and dsRNA Thereof Based on the nucleotide sequence SEQ ID No. 1 of a *Macrobrachium nipponense* Cathepsin L gene, an NCBI online dsRNA primer design software (https://www.flyrnai.org/cgi-bin/RNAi_find_primers.pl) was used in its open reading frame to design specific primers for RNA interference (SEQ ID No. 4, SEQ ID No. 5, SEQ ID No. 6 and SEQ ID No. 7), and a T7 promoter sequence of TAATACGACTCACTATAGGG, SEQ ID No. 9, which is hereby incorporated by reference in its entirety, was added before the primers. An upstream primer SEQ ID No. 4 and a downstream primer SEQ ID No. 5 as well as an interference upstream primer SEQ ID No. 6 and a downstream primer SEQ ID No. 7 containing the T7 promoter were used to obtain PCR products (sequences as shown in SEQ ID No. 3 and SEQ ID No. 8) by PCR amplification, after purification by a PCR product purification kit, according to the manufacturer's instructions, a Transcript Aid™ T7 High Yield Transcription kit (Fermentas, Inc., USA) was used for in vitro transcription to synthesize dsRNA1 and dsRNA2; 1.2% agarose gel electrophoresis was used to detect purity and integrity of dsRNA1 and dsRNA2; the concentration of the dsRNA1 and the dsRNA2 was measured with a UV spectrophotometer (Eppendorf, Hamburg, Germany) at 260 nm; and the dsRNAs were stored at −80° C. for later use.

Example 3 Experiment of Injecting dsRNA1 and dsRNA2 Synthesized by Cathepsin L Gene Fragment to Inhibit Ovary Development of Female *Macrobrachium nipponense*

(1) Injection of dsRNA1 and dsRNA2 Synthesized by Cathepsin L Gene Fragment

According to appearance characteristics of ovary development of *Macrobrachium nipponense*, 180 healthy *Macrobrachium nipponense* (0.61±0.14 g) at an ovary development stage I (white and transparent at an oogonia proliferation stage) were selected to ensure consistency of an initial ovary development period; and the *Macrobrachium nipponense* injected with dsGFP was set as a control group, while the *Macrobrachium nipponense* injected with dsRNA1 and dsRNA2 were set as experimental groups. The dsRNA synthesized in vitro was injected into the pericardial cavity of the *Macrobrachium nipponense* with a microsyringe at a dose of 4 µg/g, and 60 *Macrobrachium nipponense* were set in each group, where three parallel replicates (n=20) were set. Before injection, the *Macrobrachium nipponense* were temporarily cultured in a glass tank for three days to adapt to the laboratory culture environment (at the water temperature of 25±1° C.) and fed with fresh margarya melanoide every day in the morning and evening.

(2) Detection of Cathepsin L Gene Silencing Efficiency

On the 1st, 4th, and 7th days after the injection, 3 *Macrobrachium nipponense* were randomly collected from each group and the ovary and hepatopancreas were dissected. Total RNA was extracted using an RNAiso Plus reagent (TaKaRa, Japan) and a template cDNA was obtained by reverse transcription using a Primer ScriptII1st Strand cDNA Synthesis reverse transcription kit (Bio-Rad) and an M-MLV kit (TaKaRa, Japan). The relative expression of the Cathepsin L was detected by Real Time PCR using the template, and β-Actin was used as an internal reference gene to calculate the silencing efficiency of the target gene.

TABLE 1

Original data of hepatopancreas

| Day/Group | 1 | 4 | 7 |
|---|---|---|---|
| Control group | 2435.50 | 2929.96 | 3455.85 |
| | 2336.28 | 2991.53 | 3774.80 |
| | 2241.11 | 3228.54 | 3639.40 |
| dsRNA1 | 2215.37 | 1.05 | 17.39 |
| | 1969.12 | 0.95 | 16.22 |
| | 2154.79 | 1.00 | 14.93 |
| dsRNA2 | 2345.78 | 2987.32 | 3512.34 |
| | 2412.45 | 2887.98 | 3487.05 |
| | 2278.21 | 3098.32 | 3698.07 |

TABLE 2

Mean value and standard deviation

| Day/Group | 1 | 4 | 7 |
|---|---|---|---|
| Control group | 2337.63 ± 97.20a | 3050.01 ± 157.65b | 3623.35 ± 160.08d |
| dsRNA1 | 2113.09 ± 128.31a | 1.00 ± 0.05c | 16.18 ± 1.23c |
| dsRNA2 | 2345.48 ± 67.12a | 2991.21 ± 105.22b | 3565.82 ± 115.23d |

TABLE 3

Original data of ovary

| Day/Group | 1 | 4 | 7 |
|---|---|---|---|
| Control group | 74.54 | 391.63 | 528.83 |
| | 68.12 | 388.92 | 384.45 |
| | 88.03 | 443.67 | 392.53 |
| dsRNA1 | 82.33 | 20.30 | 1.10 |
| | 94.57 | 18.29 | 1.10 |
| | 80.63 | 15.71 | 0.84 |
| dsRNA2 | 75.32 | 389.25 | 387.56 |
| | 69.89 | 398.32 | 378.98 |
| | 86.56 | 376.21 | 369.54 |

TABLE 4

Mean value and standard deviation

| Day/Group | 1 | 4 | 7 |
|---|---|---|---|
| Control group | 76.90 ± 10.16$^a$ | 408.07 ± 30.86$^b$ | 435.27 ± 81.13$^b$ |
| dsRNA1 | 85.85 ± 7.61$^a$ | 18.10 ± 2.30$^c$ | 1.01 ± 0.15$^c$ |
| dsRNA2 | 77.26 ± 8.50$^a$ | 387.93 ± 11.11$^b$ | 378.69 ± 9.01$^b$ |

FIG. 1 and Tables 1-4 show the mRNA expression of the Cathepsin L gene in the ovary and the hepatopancreas at different sampling time points after injection of the dsGFP, the dsRNA1 and the dsRNA2 in female *Macrobrachium nipponense* at the ovary development stage I. 1, 4 and 7 were the 1st, 4th, and 7th days after the injection respectively (n=9). Different letters represented p<0.05. A green fluorescent protein (GFP) gene was used as a reporter gene in the control group and the *Macrobrachium nipponense* in the control group was injected with the same dose of dsGFP.

The results showed that compared with the dsGFP control group, the silencing efficiencies were 99.97% and 99.55% respectively in the hepatopancreas and 95.56% and 99.79% respectively in the ovary in the dsRNA1 experimental group on the 4th and 7th days after injection, while the silencing efficiencies showed no significant differences between the dsRNA2 experimental group and the control group (p>0.05).

(3) Changes of Gonadosomatic Index (GSI) of *Macrobrachium nipponense* after Injection of dsGFP, dsRNA1 and dsRNA2

TABLE 5

Original date of gonadosomatic index (GSI)

| Day/Group | 1 | 30 |
|---|---|---|
| Control group | 1.60% | 4.01% |
| | 2.38% | 3.74% |
| | 1.50% | 3.90% |
| dsRNA1 | 1.45% | 1.94% |
| | 2.38% | 1.59% |
| | 2.08% | 1.74% |

TABLE 5-continued

Original date of gonadosomatic index (GSI)

| Day/Group | 1 | 30 |
| --- | --- | --- |
| dsRNA2 | 2.20% | 4.11% |
|  | 1.45% | 3.97% |
|  | 2.10% | 3.91% |

TABLE 6

Mean value and standard deviation

| Day/Group | 1 | 30 |
| --- | --- | --- |
| Control group | 1.83% ± 0.48%$^a$ | 3.89% ± 0.13%$^b$ |
| dsRNA1 | 1.97% ± 0.48%$^a$ | 1.76% ± 0.17%$^a$ |
| dsRNA2 | 1.90% ± 0.41%$^a$ | 4.00% ± 0.10%$^b$ |

Figure 2:
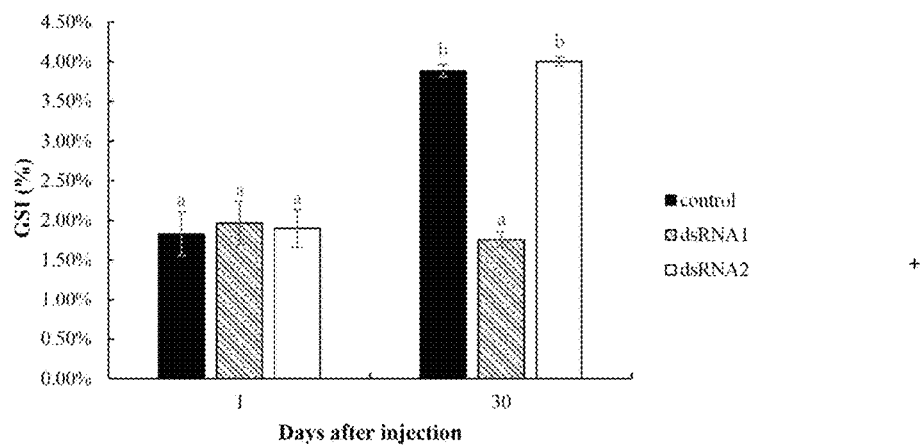
FIG. 2 is a graph showing changes of an ovary gonadosomatic index of the female *Macrobrachium nipponense* at the ovary development stage I after injection with dsGFP, dsRNA1 and dsRNA2; 1 and 30 are the 1st and 30th days after injection respectively (n=9); and different letters a and b represent $p<0.05$.

FIG. 2 and Tables 5-6 show a graph showing changes of the ovary gonadosomatic index of the female *Macrobrachium nipponense* at the ovary development stage I after injection with the dsGFP, the dsRNA1 and the dsRNA2. 1 and 30 were the 1st and 30th days after injection respectively (n=9). Different letters a and b represented p<0.05.

According to the formula of gonadosomatic index (GSI)= wet weight of gonad/wet weight of body weight×100%, the GSI of the *Macrobrachium nipponense* in the dsGFP, dsRNA1 and dsRNA2 three groups was calculated respectively. The GSI of the control group was compared with that of the dsRNA1 injection experimental group; it was found that after the Cathepsin L is silenced, the ovary development speed of the *Macrobrachium nipponense* was significantly inhibited; after cultured for 30 days, the *Macrobrachium nipponense* in the control group developed from the ovary development stage I (GSI=1.83%, white and transparent at an oogonia proliferation stage) to an ovary development stage III (GSI=3.89%, light green at a secondary vitellogenesis phase), while the *Macrobrachium nipponense* in the dsRNA1 experimental group had the GSI of 1.76% and still remained at the stage I (white and transparent at the oogonia proliferation stage); and after cultured for 30 days, the *Macrobrachium nipponense* in the dsRNA2 experimental group had the GSI of 4.00% and developed to the stage III (light green at the secondary vitellogenesis phase), which was not significantly different compared with the control group (p>0.05). The results of the GSI showed that the exogenous injection of the dsRNA1 of the Cathepsin L could effectively inhibit the ovary development speed of the *Macrobrachium nipponense*, while the dsRNA2 did not inhibit the ovary development speed.

The above descriptions are merely preferred implementations of the present disclosure. It should be noted that a person of ordinary skill in the art may further make several improvements and modifications without departing from the principle of the present disclosure, and such improvements and modifications should be deemed as falling within the protection scope of the present disclosure.

What is claimed is:

1. A method of preparing an inhibitor, wherein the inhibitor inhibits ovary development of *Macrobrachium nipponense*, which comprises:
    providing a first and a second pair of interference primers that hybridize to a *Macrobrachium nipponense* Cathepsin L gene,
    collecting total cDNA of *Macrobrachium nipponense* as a template,
    performing PCR with the total cDNA in the presence of the first and second pair of interference primers to obtain a first and a second interference gene fragment, respectively, and
    performing RNA synthesis with the first and second interference gene fragments as templates to generate a first dsRNA and a second dsRNA;
    wherein the first dsRNA and the second dsRNA are both individually inhibitors of ovary development in *Macrobrachium nipponense*;
    wherein the nucleotide sequence of the *Macrobrachium nipponense* Cathepsin L gene is set forth in SEQ ID NO. 1; and
    wherein the amino acid sequence of the protein encoded by the *Macrobrachium nipponense* Cathepsin L gene is set forth in SEQ ID NO. 2;
    wherein the nucleotide sequences of the first and the second interference gene fragments are SEQ ID NO:3 and SEQ ID NO:8, respectively.

2. The method of claim 1, wherein the nucleotide sequences of the first and the second pair of interference primers are:
    (a) SEQ ID NO:4 as an upstream primer, and SEQ ID NO:5 as a downstream primer for the first pair of interference primers, and
    (b) SEQ ID NO:6 as an upstream primer, and SEQ ID NO:7 as a downstream primer for the second pair of interference primers.

3. The method of claim 1, wherein the ovary development in the *Macrobrachium nipponense* is inhibited by injecting the first and the second dsRNA into a pericardial cavity of a female *Macrobrachium nipponense*, thereby decreasing ovary development speed of the female *Macrobrachium nipponense*.

4. The method of claim 1, wherein the first dsRNA and the second dsRNA are generated by performing RNA synthesis separately with the first pair of interference primers with the first interference gene fragment and the second pair of PCR primers with the second interference gene fragment.

5. The method of claim 1, further comprising purifying the first dsRNA and the second dsRNA.

6. The method of claim 1, wherein each of the nucleotide sequences of the first and the second pair of interference primers further comprise in frame a T7 promoter nucleotide sequence.

* * * * *

SEQUENCE LISTING

```
<160> NUMBER OF SEQ ID NOS: 9

<210> SEQ ID NO 1
<211> LENGTH: 1173
<212> TYPE: DNA
<213> ORGANISM: Artificial Sequence
<220> FEATURE:
<223> OTHER INFORMATION: Synthetic DNA

<400> SEQUENCE: 1
ttgaaatctc ccgttcaata aacattttct ccacaactac gattctctaa tccgagactt      60
tccgcagatg aaattcctgc tcttcctctg tggtttggcc atcgctgccg ccagtcagtc     120
atgggaaagc tttaagctga cccatggcaa ggcctactcc aacgccaagg aggagctcta     180
caggaagacc attttcgaga gcaaccttaa attcgtagca gaacacaatg aacgcttccg     240
aaagggccta gtcaccttca acgtcgccat gaacagattt ggtgacttga ccacagagga     300
gtttgtagcc cagatgactg gtctgcagaa actggagagc accgagggaa tggaattcgc     360
tcacttccct gaggccccca gagctgccga tgttgactgg agaaacaagg gagctgtcac     420
tcctgtcaag gaccagggac agtgtggatc ctgctggtcc ttctctacta ctggagctct     480
agaaggcgca catttcatca aaaccggaag tctgccaagc ctctccgaac agcagctggt     540
tgattgctca aaggaaaaca gcggttgcaa cggaggagtt gtgcaatggg cctacgatta     600
cctcaagtcc tgcggaggaa gccagactga gtcttcctat ccttacgagg ctattgacaa     660
catatgccgc ttcgattcat ctcaggtggc tgccactgtg aggggataca cgaacatccc     720
ctatggcgat gaggtgactc aggcctctgc tgtccacgac gaaggtccag tcagtgtctg     780
cgtcgatgct ggacacttgt ccttccagtt gtacagctca ggtgtctact acgaaccaaa     840
ctgcaaccct cagggcatca accacgccgt gttggctgtt ggctacggaa ccgaaggcgg     900
```

-continued

```
ctccgactac tggatcatca agaactcgtg gggcagcagc tggggtgagt ctggatacat    960
gaagctcacc aggaacaaga acaaccactg cggtgttgcc acccagtctt gctacccaac   1020
cgtctaagga ttccaagaaa gtctggttgc tttattccat gaagagttat gagtatacat   1080
cgacacctta actcataaga ccatagcttg ataatcatgt ctggctttat atcttgttta   1140
tgaaaaataa agtggaatcg attaaaaaaa aaa                                1173
```

<210> SEQ ID NO 2
<211> LENGTH: 319
<212> TYPE: PRT
<213> ORGANISM: Artificial Sequence
<220> FEATURE:
<223> OTHER INFORMATION: Protein translated from synthetic DNA

<400> SEQUENCE: 2

```
Met Lys Phe Leu Leu Phe Leu Cys Gly Leu Ala Ile Ala Ala Ala Ser
1               5                   10                  15

Gln Ser Trp Glu Ser Phe Lys Leu Thr His Gly Lys Ala Tyr Ser Asn
            20                  25                  30

Ala Lys Glu Glu Leu Tyr Arg Lys Thr Ile Phe Glu Ser Asn Leu Lys
        35                  40                  45

Phe Val Ala Glu His Asn Glu Arg Phe Arg Lys Gly Leu Val Thr Phe
    50                  55                  60

Asn Val Ala Met Asn Arg Phe Gly Asp Leu Thr Thr Glu Glu Phe Val
65                  70                  75                  80

Ala Gln Met Thr Gly Leu Gln Lys Leu Glu Ser Thr Glu Gly Met Glu
                85                  90                  95

Phe Ala His Phe Pro Glu Ala Pro Arg Ala Ala Asp Val Asp Trp Arg
            100                 105                 110

Asn Lys Gly Ala Val Thr Pro Val Lys Asp Gln Gly Gln Cys Gly Ser
        115                 120                 125

Cys Trp Ser Phe Ser Thr Thr Gly Ala Leu Glu Gly Ala His Phe Ile
    130                 135                 140

Lys Thr Gly Ser Leu Pro Ser Leu Ser Glu Gln Gln Leu Val Asp Cys
145                 150                 155                 160

Ser Lys Glu Asn Ser Gly Cys Asn Gly Gly Val Val Gln Trp Ala Tyr
                165                 170                 175

Asp Tyr Leu Lys Ser Cys Gly Ser Gln Thr Glu Ser Ser Tyr Pro
            180                 185                 190

Tyr Glu Ala Ile Asp Asn Ile Cys Arg Phe Asp Ser Ser Gln Val Ala
        195                 200                 205

Ala Thr Val Arg Gly Tyr Thr Asn Ile Pro Tyr Gly Asp Glu Val Thr
    210                 215                 220

Gln Ala Ser Ala Val His Asp Glu Gly Pro Val Ser Val Cys Val Asp
225                 230                 235                 240

Ala Gly His Leu Ser Phe Gln Leu Tyr Ser Ser Gly Val Tyr Tyr Glu
                245                 250                 255

Pro Asn Cys Asn Pro Gln Gly Ile Asn His Ala Val Leu Ala Val Gly
            260                 265                 270

Tyr Gly Thr Glu Gly Gly Ser Asp Tyr Trp Ile Ile Lys Asn Ser Trp
        275                 280                 285

Gly Ser Ser Trp Gly Glu Ser Gly Tyr Met Lys Leu Thr Arg Asn Lys
    290                 295                 300

Asn Asn His Cys Gly Val Ala Thr Gln Ser Cys Tyr Pro Thr Val
305                 310                 315
```

```
<210> SEQ ID NO 3
<211> LENGTH: 193
<212> TYPE: DNA
<213> ORGANISM: Artificial Sequence
<220> FEATURE:
<223> OTHER INFORMATION: Synthetic DNA

<400> SEQUENCE: 3
gctctacagg aagaccattt tcgagagcaa ccttaaattc gtagcagaac acaatgaacg      60
cttccgaaag ggcctagtca ccttcaacgt cgccatgaac agatttggtg acttgaccac     120
agaggagttt gtagcccaga tgactggtct gcagaaactg gagagcaccg agggaatgga     180
attcgctcac ttc                                                        193

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA

<400> SEQUENCE: 4
gctctacagg aagaccattt tc                                               22

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
gaagtgagcg aattccattc c                                                21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
gcctacgatt acctcaagtc c                                                21

<210> SEQ ID NO 7
<211> LENGTH: 22
<212> TYPE: DNA
<213> ORGANISM: Artificial Sequence
<220> FEATURE:
<223> OTHER INFORMATION: Synthetic DNA

<400> SEQUENCE: 7
gtggacagca gaggcctgag tc                                               22

<210> SEQ ID NO 8
<211> LENGTH: 168
<212> TYPE: DNA
<213> ORGANISM: Artificial Sequence
<220> FEATURE:
<223> OTHER INFORMATION: Synthetic DNA

<400> SEQUENCE: 8
gcctacgatt acctcaagtc ctgcggagga agccagactg agtcttccta tccttacgag      60
```

```
gctattgaca acatatgccg cttcgattca tctcaggtgg ctgccactgt gaggggatac    120
acgaacatcc cctatggcga tgaggtgact caggcctctg ctgtccac                168

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
taatacgact cactataggg                                                20
```